United States Patent
Robert et al.

(10) Patent No.: US 9,730,673 B2
(45) Date of Patent: Aug. 15, 2017

(54) METHOD FOR RECONSTRUCTING THE GEOMETRY OF A SURFACE OF AN OBJECT VIA ECHOGRAPHIC PROBING, CORRESPONDING COMPUTER PROGRAM AND ULTRASOUND PROBING DEVICE

(71) Applicant: COMMISSARIAT A L'ENERGIE ATOMIQUE ET AUX ENE ALT, Paris (FR)

(72) Inventors: Sebastien Robert, Saint-Ouen (FR); Olivier Casula, Longpont-sur-Orge (FR); Ekaterina Iakovleva, Orsay (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 166 days.

(21) Appl. No.: 14/358,539

(22) PCT Filed: Oct. 30, 2012

(86) PCT No.: PCT/FR2012/052507
§ 371 (c)(1),
(2) Date: May 15, 2014

(87) PCT Pub. No.: WO2013/072593
PCT Pub. Date: May 23, 2013

(65) Prior Publication Data
US 2014/0330127 A1 Nov. 6, 2014

(30) Foreign Application Priority Data
Nov. 15, 2011 (FR) ..................... 11 60399

(51) Int. Cl.
*A61B 8/08* (2006.01)
*G01B 17/06* (2006.01)
(Continued)

(52) U.S. Cl.
CPC ............ *A61B 8/5207* (2013.01); *A61B 8/145* (2013.01); *A61B 8/4444* (2013.01); *A61B 8/54* (2013.01);
(Continued)

(58) Field of Classification Search
CPC ..... A61B 8/145; A61B 8/4444; A61B 8/4494; A61B 8/5207; A61B 8/54
See application file for complete search history.

(56) References Cited

U.S. PATENT DOCUMENTS 5,331,855 A   7/1994 Takashita et al.
5,750,895 A   5/1998 Chern et al.
(Continued)

FOREIGN PATENT DOCUMENTS

EP   0 486 689 A1   5/1992
FR   2 786 651 B1   10/2002

OTHER PUBLICATIONS

International Search Report issued Feb. 4, 2013 in corresponding PCT/FR2012/052507.
(Continued)

*Primary Examiner* — Baisakhi Roy
(74) *Attorney, Agent, or Firm* — Oblon, McClelland, Maier & Neustadt, L.L.P.

(57) ABSTRACT

A method for reconstructing geometry of an object surface via echographic probing, using an ultrasound probe including plural transducers, the method including: controlling the transducers to transmit towards the surface ultrasound waves having initial transmission delays between them; executing at least once a cycle of operations including receiving from the transducers intermediate measurement signals, correcting transmission delays of the transducers using intermediate measurement signals, and controlling the transducers to transmit towards the surface ultrasound waves having the
(Continued)

corrected transmission delays; receiving from the transducers final measurement signals resulting from reflection of a wavefront received simultaneously on the surface; determining specular travel times between each transducer and the surface based on the final measurement signals and the corrected transmission delays; and perform geometric reconstitution of the surface based on the determined specular travel times.

10 Claims, 8 Drawing Sheets

(51) Int. Cl.
   *G01N 29/06* (2006.01)
   *G01N 29/26* (2006.01)
   *G01N 29/44* (2006.01)
   *A61B 8/14* (2006.01)
   *A61B 8/00* (2006.01)

(52) U.S. Cl.
   CPC ......... *G01B 17/06* (2013.01); *G01N 29/0654* (2013.01); *G01N 29/262* (2013.01); *G01N 29/44* (2013.01); *A61B 8/4494* (2013.01); *G01N 2291/011* (2013.01); *G01N 2291/106* (2013.01); *G01N 2291/263* (2013.01)

(56) References Cited

U.S. PATENT DOCUMENTS

| | | | |
|---|---|---|---|
| 8,767,510 B2 | 7/2014 | Robert et al. | |
| 2004/0004906 A1* | 1/2004 | Vernet | G01S 7/52003 367/87 |
| 2005/0288580 A1* | 12/2005 | Lagrange | G01S 15/8995 600/437 |
| 2006/0058668 A1* | 3/2006 | Levrier | G01S 7/52049 600/447 |
| 2006/0195273 A1 | 8/2006 | Maurer et al. | |
| 2007/0161904 A1* | 7/2007 | Urbano | A61B 8/00 600/459 |
| 2008/0108901 A1* | 5/2008 | Baba | A61B 8/0833 600/459 |
| 2009/0178483 A1* | 7/2009 | Angelsen | A61B 8/08 73/597 |
| 2009/0234230 A1* | 9/2009 | Bercoff | G01S 7/52049 600/447 |
| 2010/0036244 A1* | 2/2010 | Angelsen | A61B 8/08 600/438 |

OTHER PUBLICATIONS

S. Robert, et al., "Méthodes Ultrasonores De Détection Et D'Imagerie Temps-Réel Implémentées Dans Les Systemes D'Acquisition M2M-Real-Time Ultrasonic Techniques Implemented in M2M Acquisition Systems", Journées Cofrend "Conférences et Exposition Sur Les Essais Non Destructifs", Conferences and exhibit on non-destructive testing, May 24, 2011, XP055037304, pp. 1-13 (with English abstract).

André Lamarre, et al., "Dynamic Focusing of Phased Arrays for Nondestructive Testing: Characterization and Application", published in the E-Journal of Nondestructive Testing and Ultrasonics. No. 9, vol. 4, Sep. 1999, 12 pages.

Caroline Holmes, et al., "Post-processing of the full matrix of ultrasonic transmit—receive array data for non-destructive evaluation", NDT&E International, vol. 38, No. 8, Dec. 2005, pp. 701-711.

Fréderic Assouline, Thése, Chapter 1, "Migration Profondeur et Demigration Pour L'Analyse De Vitesse De Migration 3D", Jul. 4, 2001, 22 pages.

Andrey E. Bazulin, et al., "Algorithms and Software Development for Welds Automated Ultrasonic Inspection Basing on Phased Arrays", published following the 10th European Conference on Non-Destructive Testing, Jun. 7-11, 2010, 11 pages.

A. Fidahoussen, et al., "Imaging of Defects in Several Complex Configurations by Simulation-Helped Processing of Ultrasonic Array Data", published in the 36th Annual Review of Progress in Quantitative Non-Destructive Evaluation, vol. 29, 2010, pp. 847-854.

Jing Liang, et al., "Ultrasonic Inspection of Thick Parts With Phased Array Dynamic Focusing", published following the 10th European Conference on Non-Destructive Testing, Jun. 7-11, 2010, 7 pages.

* cited by examiner

METHOD FOR RECONSTRUCTING THE GEOMETRY OF A SURFACE OF AN OBJECT VIA ECHOGRAPHIC PROBING, CORRESPONDING COMPUTER PROGRAM AND ULTRASOUND PROBING DEVICE

This invention relates to a method for reconstructing the geometry of a surface of an object via echographic probing using an ultrasound probe provided with a plurality of transducers. It also relates to a computer program and an ultrasound probe for the implementation of this method.

The invention applies in particular to the field of non-destructive testing of mechanical parts having a complex shape, in particular during immersion testing, wherein a mechanical part is immersed in a liquid to be probed at a distance, for example in the aeronautics sector. But it can also apply during direct contact testing between the probe and the mechanical part to be probed when it is desired to determine a complex surface of the bottom of this part. More generally, it relates to varied fields of application and can be used when it is desired to reconstruct the geometry of an object or of an interface using ultrasound waves and a multiple-transducer probe. It is for example possible to mention the medical field, that of underwater acoustics, sonar, etc.

Probing methods by electronic scanning are known for finely determining the surface that is a priori unknown of an object. Unfortunately, as these methods are based on a constraint of successive and independent processings carried out by the transducers of the probe, with each transducer having to wait, before transmitting a signal, that the preceding transducer has processed the echo of its own signal, the global processing of the surface is long. These methods consequently are not suited to on-board systems for testing at high speed. Furthermore, as these methods are based on the processing of signals coming each time from a single transducer, the surface echoes returned during an echographic probing can be of an amplitude that is insufficient to carry out reliable or complete measurements.

Therefore a "real time" method is preferred, i.e. that does not have this constraint, even if the transmissions can be carried out by the transducers by following a certain law of delays.

As such, the invention relates more particularly to a method for reconstructing the geometry of an object surface comprising the following steps:
  controlling the transducers such that they transmit towards said surface of the object ultrasound waves having initial transmission delays in relation to one another,
  executing at least once the following cycle of steps, in such a way as to obtain after at least one iteration a wavefront received simultaneously on the surface:
    receiving intermediate measurement signals from the transducers, measuring in particular echoes due to reflections of the ultrasound waves on said surface of the object,
    correcting the transmission delays of the transducers using the intermediate measurement signals and controlling the transducers such that they transmit towards said surface of the object ultrasound waves having the corrected transmission delays in relation to one another,
  receiving from the transducers final measurement signals resulting from the reflection of a wavefront received simultaneously on said surface of the object.

A method of this type is for example described in the patent application published under number US 2006/0195273 A1.

More precisely, this document describes a method wherein the cycle is executed only once and according to which the step of correcting the initial transmission delays on the basis of the intermediate measurement signals consists in proceeding in two steps: first, an estimate of the unknown surface of the object is calculated explicitly on the basis of intermediate measurement signals obtained during a first firing; then a law of delays is calculated on the basis of this contour and applied during a second firing.

More precisely also, in this document, the initial transmission delays are zero delays. At the second firing, there is therefore explicitly no correction of the initial transmission delays but the direct application of the law of delays established on the basis of the estimated surface of the object.

This "real time" method was developed for testing complex stratified composite structures, i.e. an organic resin matrix reinforced with carbon fiber fabric, and applies in particular to detecting defects of the delamination type with an orientation that is quasi parallel to the surface of the part. It makes it possible to form an incident wavefront of the same curvature as the surface of the part. The wave is then transmitted into the part at normal incidence at all points of the surface, which optimizes the detecting of defects as compared to an ultrasound transmission that is not suited to the geometry of the part. The detecting and the locating of defects are carried out by analyzing the B-scan obtained (cumulative representation of the N final measurement signals received by the N transducers of the probe). This method is particularly suited for stratified composite materials for which the folds have an orientation that is quasi parallel to the surface and participate, hence, in degrading the ultrasound wave transmitted if the latter is not suited to the geometry of the object. In addition, this principle is well suited to this problem as the defects sought are delaminations between the folds of the composite and therefore have geometries that are quasi parallel to the surface of the object. Furthermore, this method is not limited to this type of materials, it can also be applied for the testing of other materials, for example metals.

Finally, this method has been generalized for testing objects having more complex geometries and, in particular, to adapt to any type of surface, whether it be concave, convex or planar with a high inclination. Indeed, when the surface to be determined of the object has substantial variations in geometry, strong interferences between the waves transmitted by the transducers then reflected by the object subsist and again alter the B-scan, even after application of the method described in the Patent application US 2006/0195273 A1.

Therefore, in the article of S. Robert et al, entitled "Real-time ultrasonic techniques implemented in M2M acquisition systems", published on the occasion of the Cofrend Days 2011, "conferences and exhibit on non-destructive testing", from 24 to 27 May 2011 in Dunkerque (FR), more precisely in chapter 3 of this document, it is proposed to repeat the aforementioned cycle of steps in such a way as to converge via successive iterations towards a genuinely simultaneous reception of the wavefront on the surface to be determined by overcoming interferences including in the presence of a very complex surface. The B-scan obtained is then of much better quality and makes possible in particular a better detection of any defects. In general, 4 to 5 iterations of the cycle of steps can suffice to achieve suitable results regardless of the type of geometry inspected. As such, the method makes it possible to inspect the various geometries (planar with or without inclination, concave, convex) of the same object by using a single probe, for example a conventional probe with a planar geometry of its transducers.

On the other hand, due to the final law of delays applied, this B-scan gives a deformed representation of the probed object, in particular of the surface simultaneously reached by the wavefront since the latter then logically has a planar form. The raw representation of the acquisition results in the form of a B-scan does not suffice to locate and characterize a defect with precision. To do this, the method must include a knowledge of the surface of the object.

It can as such be desired to provide a method for determining a surface of an object via echographic probing that makes it possible to overcome at least part of the problems and constraints mentioned hereinabove, but that remains "real time" in the aforementioned sense.

A method for reconstructing the geometry of a surface of an object via echographic probing using an ultrasound probe provided with a plurality of transducers is thus proposed, comprising the following steps:
  controlling the transducers such that they transmit towards said surface of the object ultrasound waves having initial transmission delays in relation to one another,
  executing at least once the following cycle of steps, in such a way as to obtain after at least one iteration a wavefront received simultaneously on the surface:
    receiving intermediate measurement signals from the transducers, measuring in particular echoes due to reflections of the ultrasound waves on said surface of the object,
    correcting the transmission delays of the transducers using the intermediate measurement signals and controlling the transducers such that they transmit towards said surface of the object ultrasound waves having corrected transmission delays in relation to one another,
  receiving final measurement signals from the transducers resulting from the reflection of a wavefront received simultaneously on said surface of the object,
with this method further comprising the following steps:
  determining specular travel times between each transducer and said surface of the object on the basis of final measurement signals and of the corrected transmission delays, and
  geometric reconstitution of said surface on the basis of the determined specular travel times.

"Specular travel time" between a transducer and the surface of the object means the minimum time taken by a signal transmitted by this transducer to return in the form of an echo following a reflection against the surface of the object. The specular travel time is then significant of the shortest distance separating the transducer from the surface of the object, i.e. significant of the line segment normal to this surface and connecting it to the transducer.

As a result, by artfully using the results of the final measurement carried out by the transducers in order to determine the specular travel times linked to each transducer, according to the type of multiple-transducer probe used, linear or respectively matrix, it is possible to finely reconstitute the geometry, two-dimensional or respectively three-dimensional, of the surface detected.

Optionally, determining the specular travel times comprises:
  determining a roundtrip travel time, common to all of the transducers, of the wavefront received simultaneously on said surface of the object, and
  calculating specular travel times on the basis of this roundtrip travel time, the corrected transmission delays and reception shifts applied to the transducers.

Also optionally, the geometric reconstitution of said surface comprises:
  determining distances separating each transducer from said surface on the basis of determined specular travel times,
  calculating the coordinates of points of said surface according to the coordinates of the transducers and of the determined distances, and
  the geometric reconstitution of said surface via interpolation between these points.

Also optionally, calculating coordinates of points of said surface is based on the hypothesis that said surface is tangent to a set of spheres centered respectively on the transducers and with respective radiuses corresponding to the determined distances.

Also optionally, the transducers are arranged linearly and the geometric reconstitution of said surface comprises reconstituting a profile of this surface in the test plane de the probe.

"Test plane of the probe", which is a terminology known in the field of non-destructive testing, means the main transmission plane of the transducers.

Also optionally, N transducers are arranged linearly, with the coordinates of their centers able to be expressed in the form $(c_n, 0)$ in a reference frame $(O, x, y)$ linked to the probe, and wherein the coordinates $(x_n, y_n)$ of said points of said surface are calculated using the following relationship:

$$\forall n, 1 \leq n \leq N-1, \begin{cases} x_n = c_n - d_n \cdot d'_n \\ y_n = d_n \sqrt{1-(d'_n)^2} \end{cases}, \text{where}$$

$$d'_n = \frac{d_{n+1} - d_n}{c_{n+1} - c_n}$$

and $d_n$ designates the distance separating the n-th transducer from said surface.

Also optionally, the transducers are arranged two-dimensionally in a matrix and the geometric reconstitution of said surface comprises a three-dimensional reconstitution of this surface.

Also optionally, the geometric reconstitution of said surface is accomplished via linear or bilinear interpolation between said points.

The invention also refers to a computer program that can be downloaded from a communications network and/or recorded on a support that can be read by a computer and/or be executed by a processor, comprising instructions for the executing of the steps of a method for reconstructing the geometry of a surface of an object via echographic probing according to the invention, when said program is executed on a computer.

Finally, the invention also refers to an ultrasound probing device comprising:
  a probe comprising a case and a plurality of ultrasound transducers attached to the case,
  means of controlling and of processing designed to implement a method for reconstructing the geometry of a surface of an object according to the invention.

The invention shall be better understood using the following description, provided solely by way of example and made in reference to the annexed drawings wherein.

Figure 1:
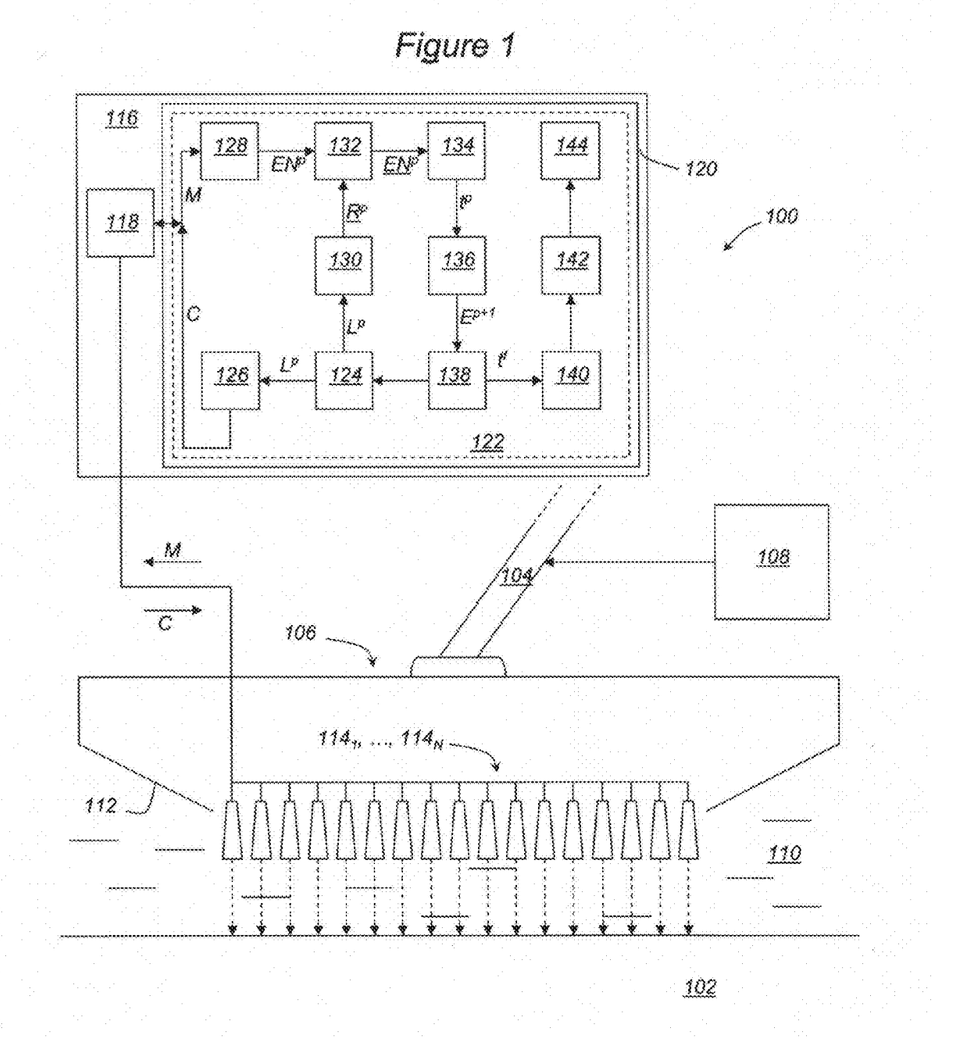
FIG. 1 diagrammatically shows the general structure of an ultrasound probing device according to an embodiment of the invention.

With reference to FIG. 1, a device for probing 100 an object 102 according to an embodiment of the invention comprises an articulated arm 104, an ultrasound probe 106 fixed to the articulated arm 104 and means 108 for controlling the articulated arm designed to control the articulated arm 104 so that the latter displaces the probe 106 in relation to the object 102.

The object 102 is for example a mechanical part that one desires to examine via non-destructive testing or, in a medical context, a portion of the human body that one desires to test in a non-invasive manner.

In the embodiment of FIG. 1, the object 102 is immersed in a liquid, such as water 110, and the probe 106 is maintained at a distance from the object 102 so that the water 110 separates them.

The probe 106 comprises first a case 112, i.e. an element with a non-deformable structure which is used as a referential attached to the probe 106.

The probe 106 further comprises N transducers $114_1, \ldots, 114_N$ arranged linearly in the case 112 and attached to the latter. The transducers $114_1, \ldots, 114_N$ are designed to transmit ultrasound waves in the direction of the object 102 in response to control signals identified under the general reference C, according to main directions parallel to one another, indicated by dotted arrows in FIG. 1, and in a main plane which is that of the figure.

The transducers $114_1, \ldots, 114_N$ are furthermore designed to detect echoes of ultrasound waves reflecting on and in the object 102 and to provide measurement signals identified under the general reference M and corresponding to these echoes.

The probing device 100 further comprises an electronic circuit 116 for controlling the transducers $114_1 \ldots 114_N$ of the probe 106 and for processing measurement signals M. The electronic circuit 116 is connected to the probe 106 so as to transmit to it the control signals C and so as to receive the measurement signals M. The electronic circuit 116 is for example that of a computer. The electronic circuit 116 has a central processing unit 118, such as a microprocessor designed to transmit towards the probe 106 the control signals C and to receive from the probe 106 the measurement signals M, and a memory 120 wherein a computer program 122 is recorded.

The computer program 122 comprises a cycle of instructions 124 to 138 that can be executed one or several times. In the rest of the description, an iteration rank p will be used to distinguish the various iterations of the cycle of instructions 124 to 138. The initial execution of the cycle corresponds to p equal to zero (first iteration), while each repetition of the cycle corresponds to the value of p:p is equal to one for the first repetition (i.e. the second iteration), to two for the second repetition (i.e. the third iteration), etc.

The computer program 122 first comprises instructions 124 designed to determine transmission delays $L^p = \{L_1^p, \ldots, L_N^p\}$, where $L_n^p$ is the transmission delay to apply to the transducer $114_n$, on the basis of initial delays $E^0 = \{E_1^0, \ldots, E_N^0\}$ and, where applicable, additional transmission delays $E^1 = \{E_1^1, \ldots, E_N^1\}, \ldots, E^p = \{E_1^p, \ldots, E_N^p\}$ that will have been determined by the instructions 136 described further on. In the embodiment described, the transmission delays $L^p$ are determined by adding the initial delays $E^0$ and the additional transmission delays $E^1, \ldots, E^p: L^p = E^0 + E^1 + \ldots + E^p$. At the first execution of the instructions 124, i.e. when p is equal to zero, the transmission delays $L^0$ are equal to the initial delays $E^0: L^0 = E^0$. The initial delays $E^0$ are predefined in the computer program 122. These are for example zero delays (no delay between the transducers $114_1, \ldots, 114_N$), in particular in the case where no information, even approximate, is known on the geometry of the object 102. Alternatively, the initial delays $E^0$ can be non-zero, and generate for example a wavefront that is partially adapted to the geometry of the object 102 as a first approximation. This alternative is for example used in the case where the geometry of the object 102 is already at least partially known.

The computer program 122 further comprises instructions 126 designed to control the transducers $114_1, \ldots, 114_N$ such that they transmit towards the object 102 ultrasound waves having transmission delays $L^p$ in relation to one another. To this effect, the instructions 126 are designed to transmit at the p-th iteration control signals C noted as $C^p = \{C_1^p, \ldots, C_N^p\}$ to the transducers $114_1, \ldots, 114_N$, where $C_n^p$ is the command transmitted to the transducer $114_n$ that has to have a transmission delay $L_n^p$. These control signals $C^p$ are designed such that the transducers $114_1, \ldots, 114_N$ each transmit a pulsed ultrasound wave with pseudo-time period T, the pulses being thus shifted in time in relation to one another with the transmission delays $L^p$. The transmission delays $L^p$ have for purpose to offset the differences between the distances separating each transducer from the object 102 for the outgoing journey, so that the ultrasound waves transmitted by the transducers $114_1, \ldots, 114_N$ reach the object 102 at the same instant.

The computer program 122 further comprises instructions 128 designed to receive at the p-th iteration, from the transducers, measurement signals M noted as $M^p=\{M_1^p, \ldots, M_N^p\}$, where $M_n^p$ is the measurement signal supplied by the transducer $114_n$, measuring in particular the echoes due to the reflections of the ultrasound waves on the object 102. The instructions 128 are furthermore designed to record the measurement signals $M^p$. In the embodiment described, the instructions 128 are designed to record the measurement signal $M_n^p$ of each transducer $114_n$ on a time gate of a predetermined duration and starting, for example, when the control signal $C_n^p$ of this transducer $114_n$ is transmitted. The records of the measurement signals $M^p$ are noted as $EN^p=\{EN_1^p, \ldots, EN_N^p\}$, where $EN_n^p$ is the recording of the signal $E_n^p$ of the transducer $114_n$. Since the control signals $C^p$ include the transmission delays $L^p$, the records $EN^p$ of measurement signals $M^p$ also integrate these transmission delays.

The computer program 122 further comprises instructions 130 designed to determine reception shifts $R^p=\{R_1^p, \ldots, R_N^p\}$ of records $EN^p$, on the basis of transmission delays $L^p$, $R_n^p$ being the reception shift of the record $EN_n^p$. In the embodiment described, the reception shifts $R^p$ are determined by means of the following formula: $R_n^p = \max(L_1^p, \ldots, L_N^p) - L_n^p$. The reception shifts $R^p$ have for purpose to offset the differences between the distances separating each transducer from the object for the return journey, so that the ultrasound waves, which are assumed to reflect at the same instant on the surface of the object 102 thanks to the transmission delays $L^p$, are synchronized and therefore considered in the record as reaching the transducers $114_1, \ldots, 114_N$ at the same instant.

The computer program 122 therefore comprises instructions 132 designed to shift the records $EN^p$ of the measurement signals $M^p$ according to the reception shifts $R^p$. The records sifted as such are noted as $\underline{EN}^p=\{\underline{EN}_1^p, \ldots, \underline{EN}_N^p\}$, where $\underline{EN}_n^p$ is the shifted record of the signal $M_n^p$ of the transducer $114_n$.

The computer program 122 further comprises instructions 134 designed to determine roundtrip travel times $t^p=\{t_1^p, \ldots, t_N^p\}$, where $t_n^p$ is the roundtrip travel time determined on the basis of shifted record $\underline{EN}_n^p$ corresponding to the transducer $114_n$. As such, the roundtrip travel times $t^p$ take into account transmission delays $L^p$ and reception shifts $R^p$. In the embodiment described, the roundtrip travel time $t_n^p$ for each transducer $114_n$ is determined by detecting, for example, the maximum envelope of the corresponding measurement signal $M_n^p$, recorded in the shifted record $\underline{EN}_n^p$.

The computer program 122 further comprises instructions 136 designed to determine new additional transmission delays $E^{p+1}$ on the basis of roundtrip travel times $t^p$. In the embodiment described, the additional transmission delays $E^{p+1}$ are determined by means of the following formula:

$$E_n^{p+1} = \frac{1}{2}[\max(t_1^p, \ldots, t_N^p) - t_n^p].$$

The computer program 122 further comprises instructions 138 designed to evaluate a stop test, in order to exit the cycle of instructions 124 to 138 if the stop test is verified or to continue with another iteration in the opposite case. In this latter case, the instructions 138 are designed to return to the instructions 124 in order to provoke another iteration of the cycle of instructions 124 à 138, with the new additional transmission delays $E^{p+1}$, in such a way that all of the additional transmission delays include the p+1 additional transmission delays $E^1, \ldots, E^{p+1}$. In this description, it is at this moment that the index p is incremented by one unit, in such a way that all of the additional transmission delays are at this moment noted as $E^1, \ldots, E^p$, in accordance with the description of the instructions 124. In the embodiment described, the stop test consists in verifying that the following inequality is verified:

$$\max(E_1^p, \ldots, E_N^p) \le \frac{\lambda}{4v},$$

where $\lambda$ is the wavelength in the water at the central operating frequency f of the transducers ($\lambda=v/f$), where v is the speed of propagation of the ultrasound waves in this same medium and where $E^p$ are the latest additional transmission delays determined by the instructions 136 (where they were noted as $E^{p+1}$). Concretely, this test means that, if the maximum difference between the roundtrip travel times $t^p$ determined by the instructions 134 is less than $$\lambda/4v,$$

then it can be considered as a first approximation that these travel times are equal and that the surface of the object 102 was indeed reached simultaneously by all of the waves transmitted. Alternatively, the instructions 138 can be designed to exit the cycle of instructions 124 to 138 after a predetermined number of executions of the cycle, for example four or five, i.e. p equal to three or four.

If the result of the stop test commands to exit the cycle of instructions 124 to 138, then the instructions 138 are designed to move to instructions 140 for analyzing the latest roundtrip travel times calculated by the instructions 134. These latest roundtrip travel times are then noted as $t^f$.

The computer program 122 therefore comprises these instructions 140 designed first to determine a roundtrip travel time Tc common to all the transducers, for example defined by $Tc=\langle t_n^f \rangle_{1 \le n \le N}$, where $\langle \rangle$ designates the average operation. Tc is the value of the first approximation of the roundtrip travel times $t^f$ considered as all equal at the exit of the cycle of instructions 124 to 138.

Artfully, the invention takes advantage of the fact that this common value of roundtrip travel time Tc for all the transducers integrates finally the latest transmission delays applied to the transducers, noted as $L^f$, and the latest reception shifts applied to the records, noted as $R^f$. In accordance with the calculation applied for the reception shifts, it is then possible to retrieve the actual specular travel time noted as $t_n$ between each transducer $114_n$ and the surface of the object 102, thanks to the following relationship:

$$\forall n, Tc = L_n^f + t_n - R_n^f.$$

Recall that the specular travel time $t_n$ between the center of the transducer 114 and the surface of the object 102 is the minimum time taken by a signal transmitted by this transducer to return in the form of an echo following a reflection against the surface of the object. It is then significant of the shortest distance separating the transducer $114_n$ from the surface of the object 102, i.e. of the line segment normal to this surface and connecting it to the transducer $114_n$: this segment will be qualified in what follows as specular travel.

The instructions 140 are then also designed to determine, for each transducer $114_n$, the specular travel time $t_n$ that is required for it according to the following calculation:

$$t_n = Tc - L_n^f + R_n^f.$$

Alternatively, the last reception shifts $R^f$ may not be applied to the last records, which would simplify the preceding equation which would then become:

$$t_n = Tc - L_n^f.$$

Finally, the instructions 140 are designed to determine, for each transducer $114_n$, the distance $d_n$ that separates it from the surface of the object 102, according to the following relationship:

$$d_n = \frac{1}{2} v \cdot t_n,$$

where v is the propagation speed of the ultrasound waves in the water.

The computer program 122 further comprises instructions 142 designed to calculate, in a reference frame (O, x, y) linked to the case 112 of the probe and defining its test plane, the coordinates $(x_n, y_n)$ of the points $P_n$ of the surface of the object 102 located at the ends of the specular travels associated with the transducers $114_n$. These points $P_n$ are defined as being part of the surface of the object 102 (more precisely of its intersection with the test plane) and circles (as intersections of spheres with the test plane) respectively centered on the transducers and with radiuses $d_n$: in other terms, the surface of the object 102 such as shown in the test plane of the probe is naturally defined as being a curve tangent to the set of respective circles of centers $C_n$ (i.e. the punctual centers of each transducer $114_n$) and of radii $d_n$, or in other words as the envelope of these circles. A method for resolving this purely geometrical problem is for example provided in the document of F. Assouline, entitled "Migration profondeur et denigration pour l'analyse de vitesse de migration 3D", constituting a thesis defended at the University of Pau and of the Pays de l'Adour, Doctoral school of exact sciences and their applications, on 4 Jul. 2001. More particularly in chapter 1.3.4 entitled "Migration 3D de Kirchhoff par deport commun", the determining of an envelope of isochrones is given by a system of equations 1.72 that can be simplified on a case-by-case basis according to the embodiment chosen.

As such for example, in the two-dimensional case of a probe where the N transducers are arranged linearly in the case 112, the coordinates of their centers can be expressed in the form $(c_n, 0)$ in the reference frame (O, x, y) and the equation system 1.72 applied to the points $P_n$ by the instructions 142 is simplified in the following way:

$$\forall n, 1 \leq n \leq N-1, \begin{cases} x_n = c_n - d_n \cdot d_n' \\ y_n = d_n \sqrt{1 - (d_n')^2} \end{cases}, \text{ where}$$

$$d_n' = \frac{d_{n+1} - d_n}{c_{n+1} - c_n}.$$

Note that with a probe with N transducers, the surface to be detected is described by N−1 points $P_n$, with the calculation of the discrete derivatives $d_n'$ not making it possible to know the last point of the surface.

The computer program 122 further comprises instructions 144 designed to geometrically reconstitute the surface to be detected via a linear interpolation. This approximation is valid for objects that do not have surface variations that are too abrupt between two successive transducers of the probe, which is true in most of the applications where the tested surfaces are slowly variable. Alternatively, the linear interpolation can be replaced with a polynomial interpolation. In the case of a probe with N transducers arranged linearly, it is a profile of the surface of the object 102 in the test plane of the probe which is as such obtained.

But the instructions 142 and 144 can easily be adapted to a matrix probe wherein the transducers are arranged two-dimensionally in a matrix. In this case, the principle of the geometric reconstitution of the surface of the object 102 consists more generally in calculating the surface tangent to a family of spheres of radiuses $d_i$ and of which the centers $C_i$ are the centers of the transducers of the matrix.

In reference to FIG. 2, a method 200 for determining the surface of the object 102 implemented by the device 100 of FIG. 1 shall now be described.

During a step 202, the processing unit 118 executing the instructions 124 determines the transmission delays $L^P = \{L_1^P, \ldots, L_N^P\}$ on the basis of the initial delays $E^0$ and, where applicable, additional transmission delays $E^1, \ldots, E^P$ which will have been determined in the step 222 described further on.

During steps $204_1$ à $204_N$, the processing unit 118 executing the instructions 126 controls each transducer $114_n$ such that it transmits ultrasound waves towards the object 102, with the ultrasound waves transmitted by the transducers $114_1, \ldots, 114_N$ having the transmission delays $L^P$ in relation to one another. To this effect, the processing unit 118 executing the instructions 126 transmits each control signal $C_n^P$ to the corresponding transducer $114_n$, with the control signals $C^p$ including the transmission delays $L^P$.

During steps $206_1$ à $206_N$, the processing unit 118 executing the instructions 128 starts, following the transmission of each control signal $C_n^P$ towards the corresponding transducer $114_n$, the record of the measurement signal $M_n^P$ supplied by this transducer $114_n$.

During steps $208_1$ to $208_N$, each transducer $114_1, \ldots, 114_N$ transmits, following the reception of its control signal, a pulsed ultrasound wave with central frequency f. As such, the pulses are shifted in time in relation to one another of the transmission delays $L^P$.

During steps $210_1$ to $210_N$, each transducer $114_n$ receives the echoes of the ultrasound waves reflected on and in the object 102.

During steps $212_1$ to $212_N$, each transducer $114_n$ provides its measurement signal $M_n^P$, measuring in particular the echoes of the ultrasound waves on the surface of the object 102. The processing unit 118 executing the instructions 128 receives this signal $M_n^P$ and records it in the record $EN_n^P$.

During steps $214_1$ to $214_N$, the processing unit 118 executing the instructions 128 stops the recording $EN_n^P$ of the signal $M_n^P$ of the transducer $114_n$.

During a step 216, the processing unit 118 executing the instructions 130 determines the reception shifts $R^P$ on the basis of transmission delays $L^P$.

During a step 218 the processing unit 118 executing the instructions 132 shifts the records $EN^P$ of the measurement signals $M^P$ according to the reception shifts $R^P$, in order to obtain the shifted record $\underline{EN}^P$.

During a step 220, the processing unit 118 executing the instructions 134 determines the roundtrip travel times $t^P = \{t_1^P, \ldots, t_N^P\}$ between the transducers $114_1 \ldots 114_N$ and the object 102 taking into account the transmission delays $L^p$ and the reception shifts $R^p$, on the basis of shifted records $\underline{EN}^p$.

During a step 222, the processing unit 118 executing the instructions 136 determines new additional transmission delays $E^{p+1}$ on the basis of roundtrip travel times $t^p$.

As such, note that the steps 216 to 222 make it possible to determine additional transmission delays $E^{p+1}$ on the basis des measurement signals $M^p$.

During a step 224, the processing unit 118 executing the instructions 138 determines the stopping or the continuing of the cycle of instructions 124 to 138, and, in this latter case, increments p by one unit before returning to the step 202.

If the stop test is verified, control passes to a step 226 during which the processing unit 118 executes the instructions 140 in order to determine the specular travel time $t_n$ associated with each transducer $114_n$.

During a following step 228, the processing unit 118 executing the instructions 140 determines on the basis of each specular travel time $t_n$, each distance $d_n$ that separates each transducer $114_n$ from the surface of the object 102.

Then, during a step 230, the processing unit 118 executing the instructions 142 determines N−1 points $P_1, \ldots, P_{N-1}$ on the surface of the object 102.

Finally, during a step 232, the processing unit 118 executing the instructions 144 geometrically reconstitutes the surface of the object 102 via interpolation, in particular via linear interpolation.

Figure 2:
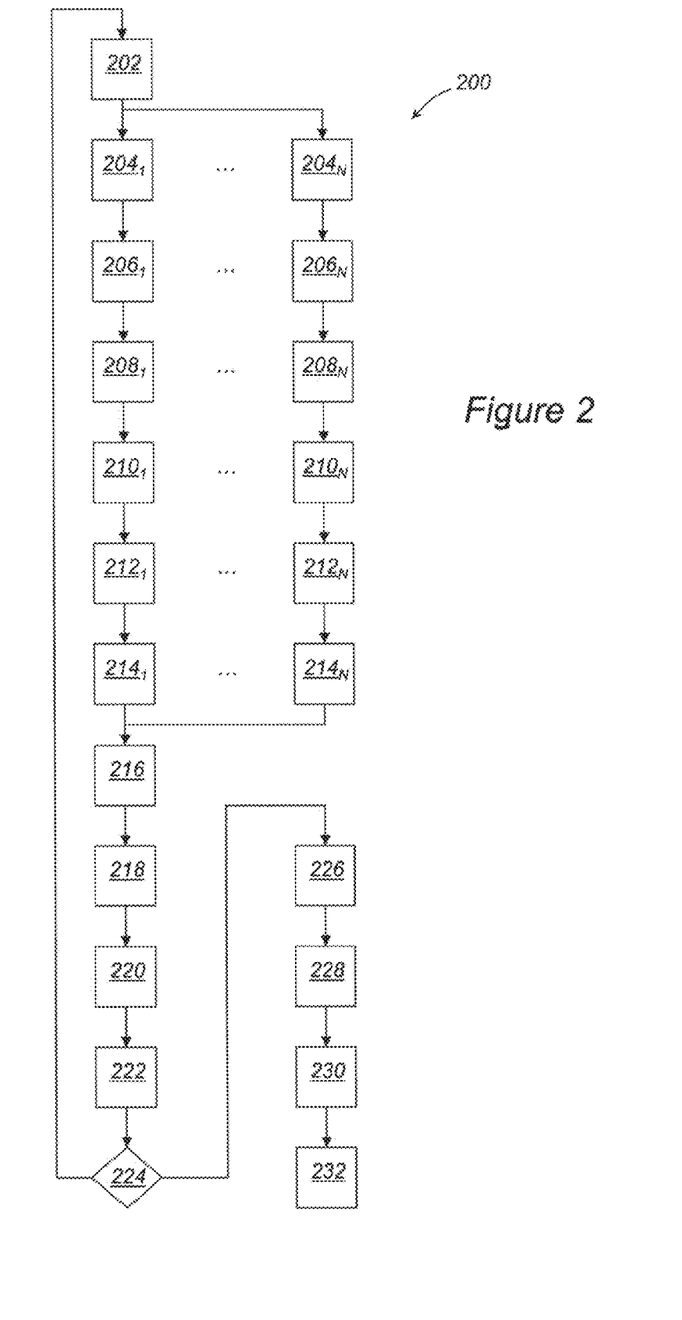
FIG. 2 shows the successive steps of a method for determining the surface of an object implemented by the probing device of FIG. 1.

The steps 226 to 232 carry out simple and therefore fast processing which does not add any significant complexity to the whole of the method of FIG. 2. As a result, the invention proposes a "real time" method for detecting the surface, even complex, of an object of which the surface condition is not known beforehand. This method can thus be qualified as adaptive allowing for real-time imaging.

The method of FIG. 2, compatible with an operation at high speed, is implemented at each position of the displacement of the probe 106 in relation to the object 102. In the case where the object has low variations in geometry along this displacement, the initial transmission delays $E^0$ at a given position are advantageously taken equal to the latest transmission delays $L^p$ determined at a preceding position, in particular the immediately preceding position. This makes it possible to increase the inspection speeds of parts with a very extensive surface by decreasing the number of firings at each position.

With reference to FIGS. 3 to 9, details of a first example of use of the method for determining the surface of FIG. 2 shall be provided.

Figure 3:
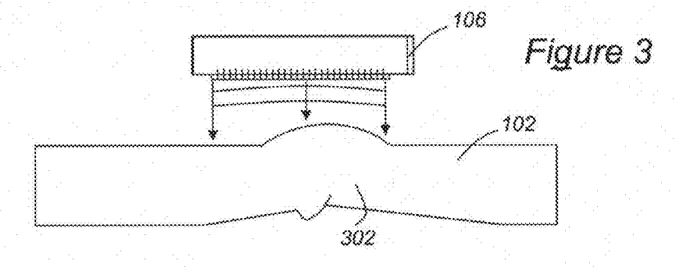
FIG. 3 shows a first example of the use of the probe of FIG. 1 to probe an object of which the geometry is representative of a welding bead.

With reference to FIG. 3, in the example described, the object 102 is a metal part of which the complex geometry is representative of a welding bead 302 that the probe 106 of the probing device 100 is intended to probe. The probe 106 comprises for example N=128 transducers.

In order to probe the welding bead 302, the method of FIG. 2 is implemented.

At a first execution of the cycle of steps, i.e. when p is equal to zero (first iteration), ultrasound waves are transmitted at steps $208_1$ to $208_N$ by the transducers with transmission delays $L^0$ equal to the initial delays $E^0$: $L^0 = E^0$, zero in the example described.

Figures 4, 5, 6, 7:
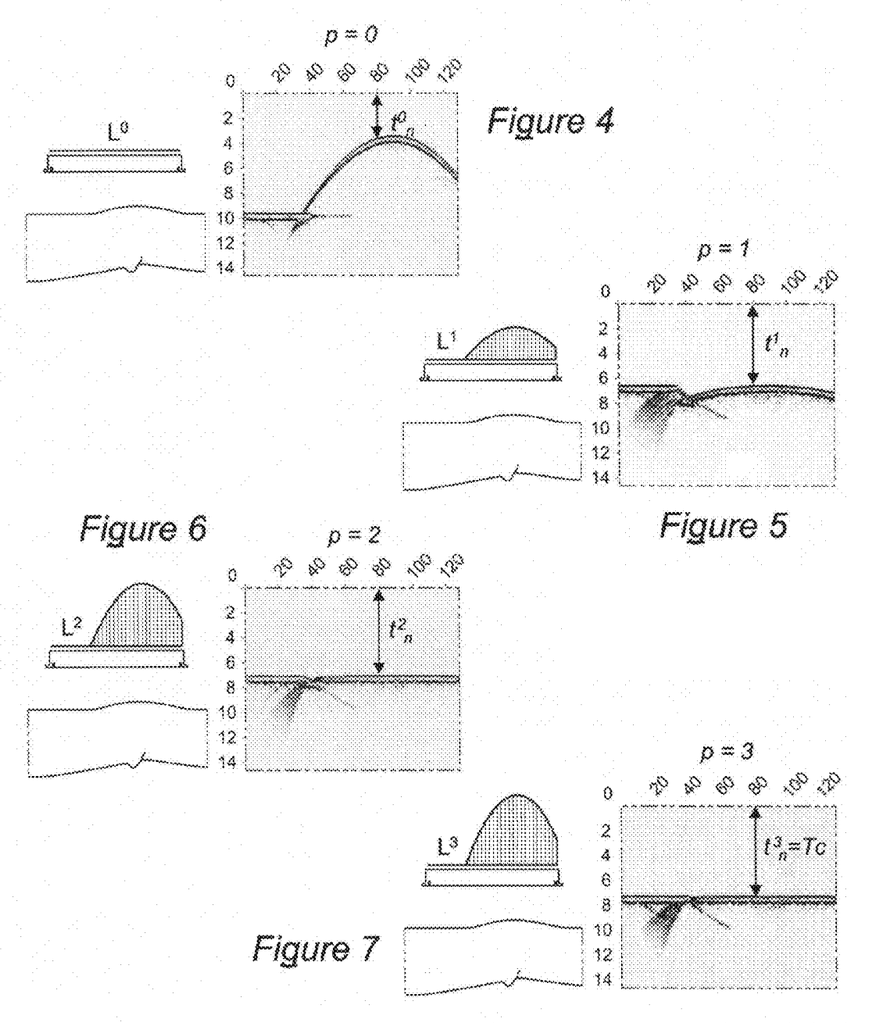
FIGS. 4 to 7 are B-scans obtained on the basis of measurement signals on the object with a welding bead of FIG. 3, for respectively a first, a second, a third and a fourth iteration of a cycle of steps of the method of FIG. 2, FIGS. 8A, 8B and 8C show, using diagrams and a cross-section view of the object with a welding bead of FIG. 3, the operation of the steps of calculating specular travel times and paths of the method of FIG. 2.

Shifted records $\underline{EN}^p$ are then obtained in step 218. With reference to FIG. 4, the amplitude of the envelope of the shifted signals $\underline{EN}^p$ is determined in the step 220. These are shown in FIG. 4, wherein the vertical axis corresponds to the time, the axis horizontal to the transducers and the amplitude of the envelope to the level of gray of the points. This representation is known, as indicated hereinabove, under the name "B-scan". On this B-scan representation, the roundtrip distance $t_n^0$ for each transducer $114_n$ is determined as being the distance separating the origin of the times to the maximum of the amplitude of the envelope, i.e. to the darkest point on the vertical line corresponding to the transducer $114_n$.

Alternatively, note that the B-scan representation can be modified by applying a sliding average processing to the measurement signals recorded in the shifted records $\underline{EN}^p$.

The additional transmission delays $E^1$ are then determined in the step 222, and continuing the execution of the program is decided in the step 224 in such a way that a first repetition (second iteration) of the steps is carried out (p is incremented to 1).

FIG. 5 shows the B-scan obtained in the step 220 of this first repetition (or second iteration, p=1), on the basis of the transmission delays $L^1 = E^0 + E^1$. As the additional transmission delays were calculated on the basis of roundtrip travel times, it is expected to obtain a horizontal surface of the probed object that would indicate that the ultrasound waves of all of the transducers reach the welding bead 302 at the same instant. However, note that this is not the case and that the surface line, corresponding to the welding bead 302, is still somewhat bulging.

Indeed, the inventors have determined that, for parts with complex geometry, the first iteration and its repetition until the step 220 are not enough to correct the differences in geometry and the phenomena of the superposition of waves on the same measurement signal that stems from it. Indeed, each transducer detects an echo which is the product of the interference between the echo resulting from its own transmission of ultrasound waves and the echoes resulting from the ultrasound waves transmitted by the adjacent transducers. However it is possible to adapt the probing device 100 to very complex geometries, such as the welding bead 302, by fully iterating several times the steps of the method 200 of FIG. 2.

As such, FIG. 6 shows the B-scan obtained in the step 220 of the second repetition (or third iteration, p=2), on the basis of the transmission delays $L^2 = E^0 + E^1 + E^2$, while FIG. 7 shows the B-scan obtained in the step 220 of the third repetition (or fourth iteration, p=3), on the basis of transmission delays $L^3 = E^0 + E^1 + E^2 + E^3$. Note that the surface of the object probed is practically horizontal on this last figure, indicating that the probing device 100 is adapted to the geometry of the object 102, i.e. that the ultrasound wavefront formed by the set of waves generated by all the transducers $114_1 \ldots 114_N$ has the same curvature as the surface of the welding bead 302. During this last step, all of the roundtrip travel times can be considered as equal to the same value Tc.

Figure 8A:
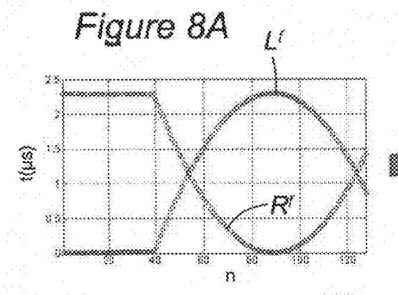
Figure 8B:
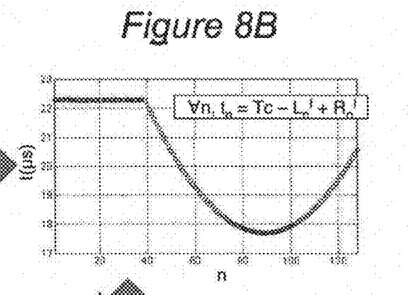
Figure 8C:
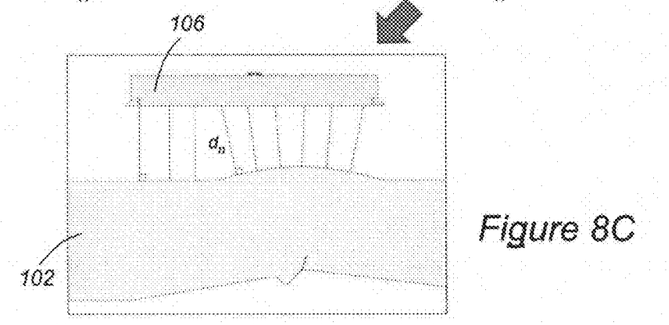

FIGS. 8A, 8B and 8C show the unfolding of the steps 226 and 228 on the execution of the instructions 140. FIG. 8A shows the last transmission delays $L^1$ applied to the N transducers and the last reception shifts $R^f$ applied to the records. FIG. 8B shows the resulting specular travel times, calculated in the step 226, for a value Tc of 20 µs. Finally, FIG. 8C shows the distances $d_n$ that separate each transducer $114_n$ from the surface of the object 102, i.e. the lengths of the specular travels such as calculated in step 228.

Figure 9:
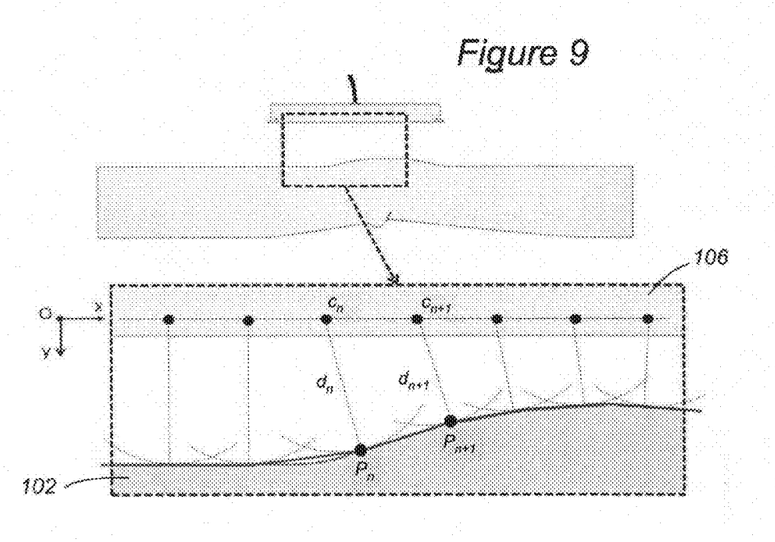
FIG. 9 shows, using a cross-section view of the object with a welding bead of FIG. 3, the operation of steps of the geometric reconstitution of the surface of the method of FIG. 2.

FIG. 9 shows the result of the steps 230 and 232 on the execution of the instructions 142 and 144. The surface of the object 102 is geometrically reconstituted via linear interpolation on the basis of points $P_n$ which are themselves determined on the basis of positions $c_n$ of the transducers $114_n$ and of the distances $d_n$.

Figure 10:
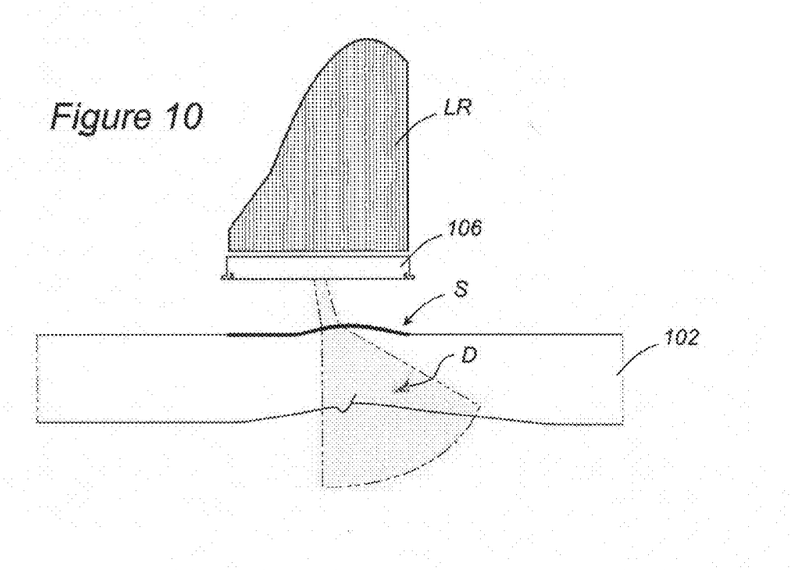
FIG. 10 shows, using a cross-section view of the object with a welding bead of FIG. 3, a first application of the method of FIG. 2.
Figure 11:
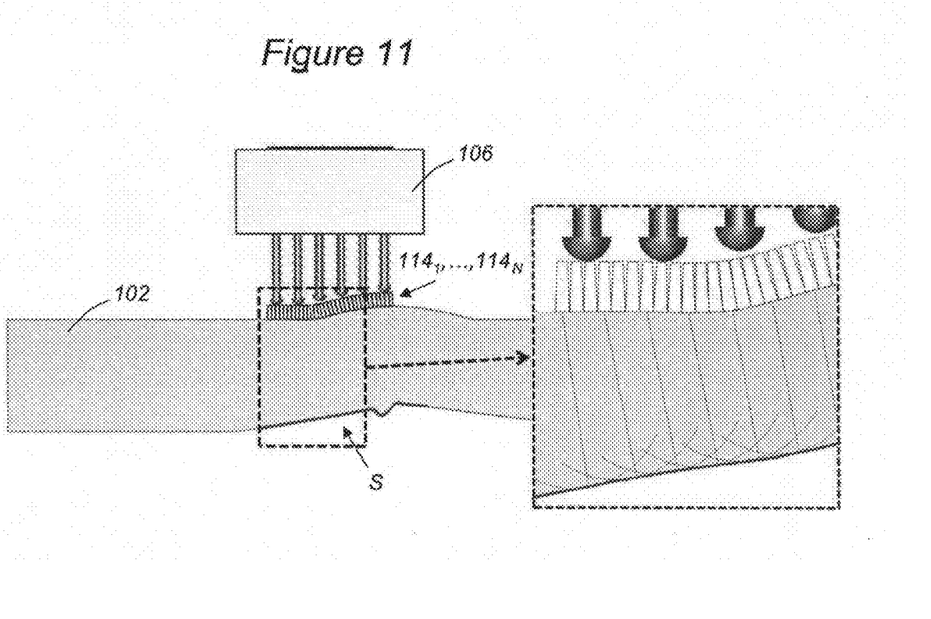
FIG. 11 shows, using a cross-section view of the object with a welding bead of FIG. 3, a second application of the method of FIG. 2.

Taking the example of FIGS. 3 to 9, wherein the object 102 is a metal part of which the complex geometry is representative of a welding bead 302, two different applications are considered and shown in FIGS. 10 and 11.

The first application of the previously-detailed method is the echographic imaging of metal parts in real time by focusing in different points. This application is shown in FIG. 10 with an S-scan image obtained by focusing according to different angles and at a constant depth. This technology is based on controlling at each instant the depth and the focusing angle of the ultrasound beam by the definition of a set of laws of delays (one law of delays for each focal point) changing over time and applied to all of the transducers of the probe. But, in prior art, this technology requires a perfect knowledge of the geometry of the probed object in order to be able to consequently adapt the laws of delays. As such, for an object with variable geometry, the test would require reconstructing the surface of the object for each position of the probe in order to adapt the laws of delays to the geometry encountered and control a constant beam all throughout the displacement and regardless of the surface state of the object probed.

A solution, provided by the application of the method of FIG. 2, is shown in FIG. 10. As can be seen, after reconstitution of the surface S of the object 102 thanks to the application of the method of FIG. 2, a set of laws of delays LR is calculated according to this reconstituted surface in order to focus according to different angles and at a constant depth. An S-scan is obtained, making it possible in particular to detect any defects D. The use of this method thus makes it possible to reconstitute the surface of the object at each position of the probe and to consequently adapt the laws of delays to control an S-scan image in real-time during displacement.

The conventional technology used for obtaining an image from a set of laws of delays adapted thanks to the application of the method of detection according to the invention is for example one of those described in the following documents:

the article by A. Lamarre and al, entitled "Dynamic focusing of phased arrays for nondestructive testing: characterization and application", published in the e-Journal of Nondestructive Testing and Ultrasonics, no. 9, vol. 4, September 1999, the article by J. Liang and al, entitled "Ultrasonic Inspection of thick parts with phased array dynamic focusing", published following the 10$^{th}$ European Conference on Non-Destructive Testing, 7-11 Jun. 2010, Moscow, the article by C. Holmes and al, entitled "Post-processing of the full matrix of ultrasonic transmit-receive array data for non-destructive evaluation", published in NDT & E International, vol. 38, no. 8, pages 701-711, December 2005, and the article by A. Fidahoussen and al, entitled "Imaging of defects in several complex configurations by simulation-helped processing of ultrasonic array data", published in the 36$^{th}$ Annual Review of Progress in Quantitative Non-Destructive Evaluation, vol. 29, pages 847-854, 2010.

The second application of the previously detailed method, shown in FIG. 11, relates to a family of applications according to which the echographic images are obtained by applying laws of delays that make it possible to focus in the part after reflection on the bottom. This requires prior knowledge of the geometry of the surface but also of the bottom of the object to be inspected, as for example mentioned in the article of A. Bazulin and al, entitled "Algorithms and software development for welds automated ultrasonic inspection basing on phased arrays", published following the 10$^{th}$ European Conference on Non-Destructive Testing, 7-11 Jun. 2010, Moscow, or in the aforementioned article of A. Fidahoussen and al. If the multiple-transducer probe is intended to be in contact with the probed object 102, only the surface of the bottom of the object 102 requires being reconstituted. Through strict application of the method of FIG. 2, this bottom surface can be geometrically reconstituted relatively to the surface which is in contact with the transducers, the sole difference residing in the speed of the ultrasound waves which, in contact, becomes that of the longitudinal waves propagating in the material of the probed object.

FIG. 11 shows in particular the case where the multiple-transducer probe is in contact with the object by using the technology described in the French patent published under number FR 2 786 651. In this document, the transducers are attached in a mobile manner to the case in order to be able to hug the geometry of the surface of the object to be probed. Means are then provided to determine the positions of the transducers, and as such the geometry of the surface of the object. The strict application of the method of FIG. 2 thus makes it possible, on the basis of the knowledge of the surface, to deduce from it the geometry of the bottom of the part.

With reference to FIGS. 12 to 16, details on a second example of use of the method for determining the surface of FIG. 2 shall now be provided. This second example relates to inspecting composite parts.

Figure 12:
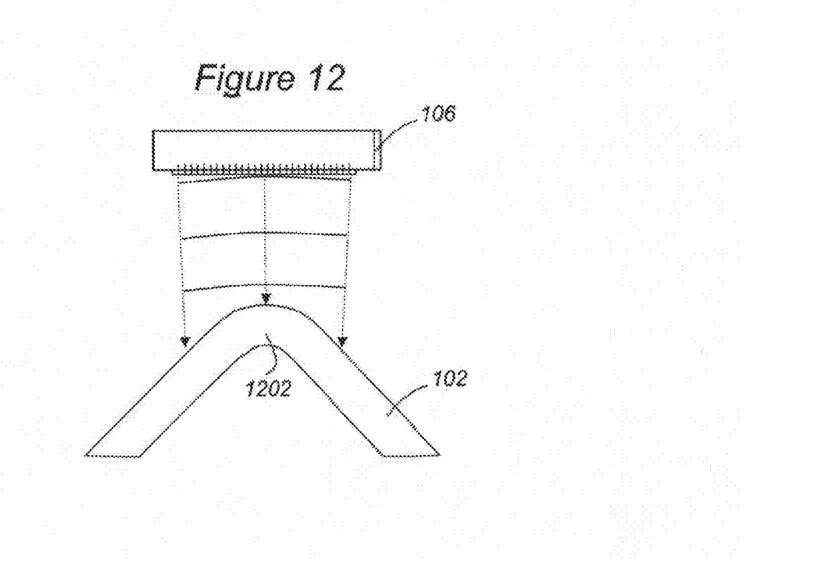
FIG. 12 shows a second example of the use of the probe of FIG. 1 for probing an object of the composite radius type.
Figure 13:
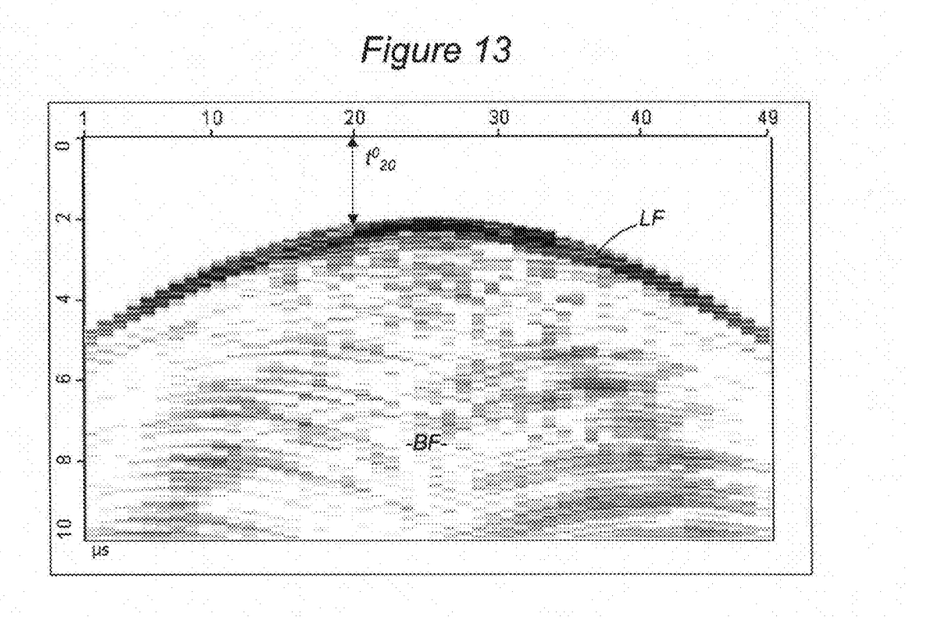
FIGS. 13 to 16 are B-scans obtained on the basis of measurement signals on the composite object of FIG. 12, for respectively a first, a second, a third and a fourth iteration of a cycle of steps of the method of FIG. 2.

With reference to FIG. 12, in the example described, the object, referenced as 102', is a part having a composite radius 1202 of a high angle that the probe 106 of the probing device 100 is intended to probe. The probe 106 comprises for example N=49 transducers.

In order to probe the composite radius 1202, the method of FIG. 2 is implemented.

At a first execution of the cycle of steps, i.e. when p is equal to zero (first iteration), ultrasound waves are transmitted in steps $208_1$ to $208_N$ by the transducers with transmission delays $L^0$ equal to the initial delays $E^0$: $L^0=E^0$, zero in the example described.

Shifted records $\underline{EN}^p$ are obtained in the step 218. In reference to FIG. 13, the amplitude of the envelope of the shifted signals $\underline{EN}^p$ is determined in the step 220 and reproduced in the corresponding B-scan. Note the appearance of a dark surface line LF, corresponding to the surface echo of the composite radius 1202, followed by a substantial structural noise BF which does not in any case make it possible to reveal the presence of any defect in the object 102'.

The additional transmission delays $E^1$ are then determined in the step 222, and the continuing of the execution of the program is decided in the step 224 in such a way that a first repetition (second iteration) of the steps is carried out (p is incremented to 1).

Figure 14:
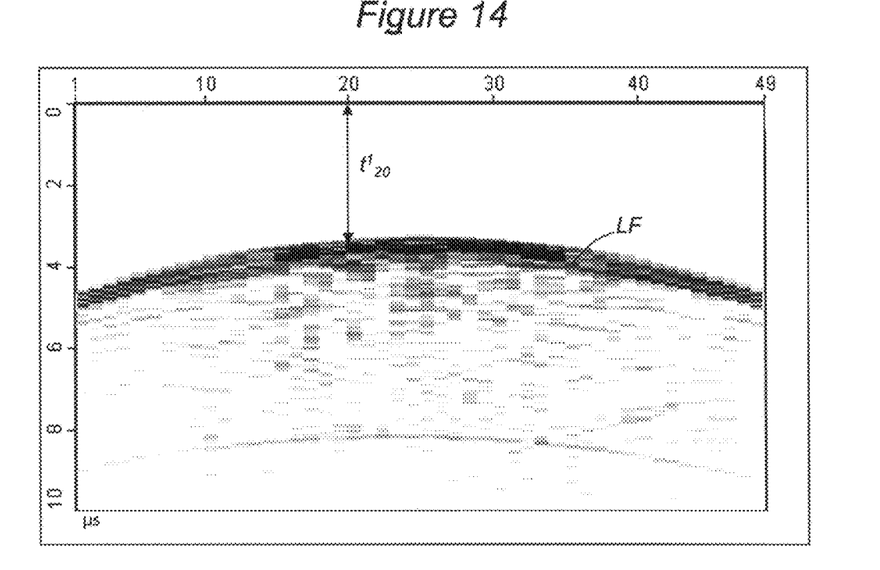

FIG. 14 shows the B-scan obtained in the step 220 of this first repetition (or second iteration, p=1), on the basis of the transmission delays $L^1=E^0+E^1$. Here again, the surface line LF of the probed object, corresponding to the surface of the composite radius 1202, is still somewhat bulging.

Figure 15:
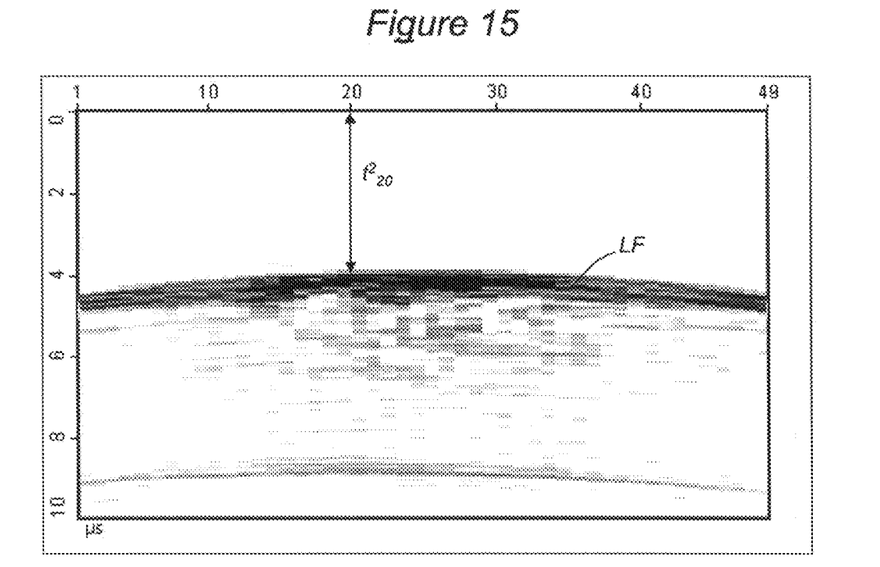
Figure 16:
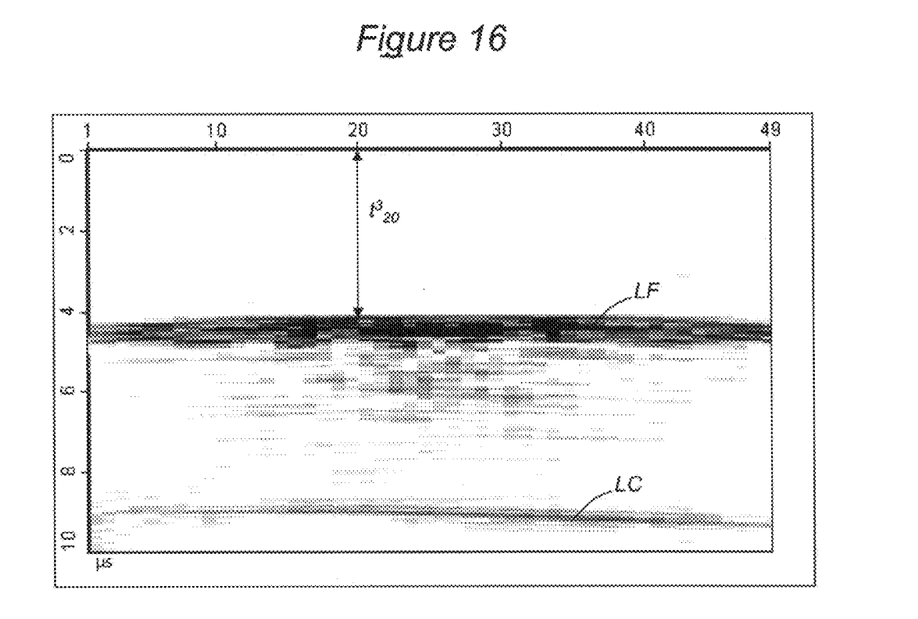

FIG. 15 shows the B-scan obtained in step 220 of the second repetition (or third iteration, p=2), on the basis of the transmission delays $L^2=E^0+E^1+E^2$, while FIG. 16 shows the B-scan obtained in the step 220 of the third repetition (or fourth iteration, p=3), on the basis of the transmission delays $L^3=E^0+E^1+E^2+E^3$.

Note that the dark line LF is practically horizontal on this latter figure, indicating that the ultrasound wavefront formed by all of the waves generated by all of the transducers $114_1 \ldots 114_N$ has the same curvature as the surface of the composite radius 1202. Furthermore, the internal noise has disappeared, allowing the real structure of the object 102' to appear, in particular a light line LC indicating the bottom of the object. As such, any defect in the object 102' is revealed thanks to a multiple repetition of the previously described cycle of steps. In particular, defaults of the delamination type are better detected.

Executing steps 226 to 232 on the result obtained in FIG. 16 thus makes it possible to geometrically reconstitute the curved surface of the object 102'.

Figure 17:
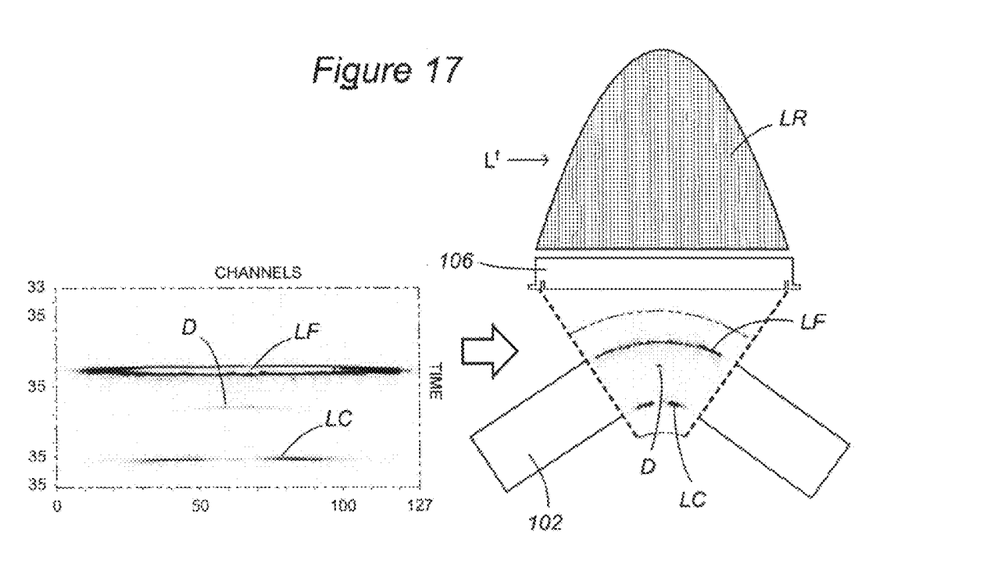
FIG. 17 shows, using a B-scan and a cross-section view of the composite object of FIG. 12, a third application of the method of FIG. 2.

Using the example in FIGS. 12 to 16, wherein the object 102' is a composite part having a composite radius 1202 with a high angle, a third application is considered and shown in FIG. 17.

This third application consists in reconstructing an echographic image using the B-scan of FIG. 16. This B-scan is shown in the left portion of FIG. 17 with a defect D detected in the object 102'. The right portion is an echographic image wherein the pixels of the left B-scan are repositioned in the reference frame (O, x, y) thanks to the knowledge of the geometry of the surface detected and in comparison with its linear form in the B-scan. Thanks to this transformation, not only is the D defect detected, but furthermore it can be located and measured with precision in the reconstructed echographic image.

Furthermore, by displacement of the probe along the object, several echographic images can be reconstructed and concatenated into a single full image of the object.

It appears clearly that a method and a device such as those described previously make it possible to finely reconstruct the geometry, two-dimensional or respectively three-dimensional, of a surface of an object detected by echography, with this fine reconstitution opening the door to improve a plurality of applications.

Note furthermore that the method described previously allows for a detection in real time and a high level of quality.

Note moreover that the invention is not limited to the previously described embodiments. It will appear to those skilled in the art that various modifications can be made to the embodiments described hereinabove, in light of the information which has just been disclosed.

In particular, the computer program instructions could be replaced with electronic circuits dedicated to the functions carried out during the execution of these instructions.

Furthermore, the method according to the invention can be implemented with a mechanical displacement of the probe or by proceeding with an electronic displacement of a sub-opening along the total opening of the sensor where the transducers are located.

In the following claims, the terms used must not be interpreted as limiting the claims to the embodiment exposed in this description, but must be interpreted to include therein all of the equivalents that the claims aim to cover due to their training and of which foreseeing this is within the scope of those skilled in the art by applying their general knowledge to the implementation of the information which has just been disclosed.

The invention claimed is:

1. A method for reconstructing a geometry of a surface of an object via echographic probing using an ultrasound probe including a plurality of N transducers, the method comprising:

controlling the N transducers to transmit, towards the surface of the object, N ultrasound waves having N initial transmission delays in relation to one another;

executing at least once a cycle of operations including:
receiving from the N transducers N intermediate measurement signals that measure N echoes due to N reflections of the N ultrasound waves on the surface of the object, correcting the N transmission delays of the N transducers using the N echoes measured in the N intermediate measurement signals, and controlling the N transducers to transmit, towards the surface of the object, N ultrasound waves having the N corrected transmission delays in relation to one another, until obtaining after the at least one cycle of operations a wavefront received simultaneously on the surface;

receiving from the N transducers N final measurement signals resulting from reflection of a wavefront received simultaneously on the surface of the object;

determining N specular travel times, each corresponding to a minimum time taken by a signal transmitted by a transducer to return to the same transducer in a form of an echo following a reflection against the surface of the object, between each transducer and the surface of the object based on the N final measurement signals and the N corrected transmission delays; and performing geometric reconstitution of the surface of the object based on the N determined specular travel times.

2. The method for reconstructing a surface geometry as claimed in claim 1, wherein the determining of the N specular travel times comprises:

determining a roundtrip travel time, common to all of the N transducers, of the wavefront received simultaneously on the surface of the object, and calculating N specular travel times based on the roundtrip travel time, the N corrected transmission delays, and N reception shifts applied to the N transducers.

3. The method for reconstructing a surface geometry as claimed in claim 1, wherein the geometric reconstitution of the surface comprises:

determining N distances separating each transducer from the surface based on the N determined specular travel times, calculating coordinates of points of the surface according to coordinates of the N transducers and of the N determined distances, and performing the geometric reconstitution of the surface via interpolation between the points.

4. The method for reconstructing a surface geometry as claimed in claim 3, wherein the calculating of the coordinates of points of the surface is based on the surface being tangent to a set of spheres centered respectively on the N transducers and with respective radiuses corresponding to the N determined distances.

5. The method for reconstructing a surface geometry as claimed in claim 3, wherein the N transducers are arranged linearly and the geometric reconstitution of the surface comprises reconstitution of a profile of the surface in a test plane of the probe.

6. The method for reconstructing a surface geometry as claimed in claim 5, wherein the N transducers are arranged linearly, with coordinates of their centers to be expressed in a form in a reference frame linked to the probe, and wherein the coordinates of the points of the surface are calculated using relationship:

$$\forall n, 1 \leq n \leq N-1, \begin{cases} x_n = c_n - d_n \cdot d'_n \\ y_n = d_n \sqrt{1 - (d'_n)} \end{cases}, \text{where}$$

$$d'_n = \frac{d_{n+1} - d_n}{c_{n+1} - c_n}$$

and $d_n$ designates the distance separating the n-th transducer from the surface.

7. The method for reconstructing a surface geometry as claimed in claim 3, wherein the N transducers are arranged two-dimensionally in a matrix and the geometric reconstitution of the surface includes a three-dimensional reconstitution of the surface.

8. The method for reconstructing a surface geometry as claimed in claim 3, wherein the geometric reconstitution of the surface is accomplished by linear or bilinear interpolation between the points.

9. A non-transitory computer readable medium including a computer program comprising instructions for execution of the method for reconstructing the geometry of a surface of an object via echographic probing as claimed in claim 1, when executed on a computer.

10. An ultrasound probing device comprising:
a probe comprising a case and a plurality of N ultrasound transducers attached to the case; and
a control and processing circuit configured to
control the N transducers to transmit towards a surface of an object N ultrasound waves having N initial transmission delays in relation to one another;
execute at least once a cycle of operations including:
receiving from the N transducers N intermediate measurement signals that measure N echoes due to N reflections of the N ultrasound waves on the surface of the object,
correcting the N transmission delays of the N transducers using the N echoes measured in the N intermediate measurement signals, and
controlling the N transducers to transmit, towards the surface of the object, N ultrasound waves having the N corrected transmission delays in relation to one another,
until obtaining after the at least one cycle of operations a wavefront received simultaneously on the surface;
receive from the N transducers N final measurement signals resulting from reflection of a wavefront received simultaneously on the surface of the object,
determine N specular travel times, each corresponding to a minimum time taken by a signal transmitted by a transducer to return to the same transducer in a form of an echo following a reflection against the surface of the object, between each transducer and the surface of the object based on the N final measurement signals and the N corrected transmission delays, and
geometrically reconstitute the surface of the object based on the N determined specular travel times.

* * * * *

UNITED STATES PATENT AND TRADEMARK OFFICE
CERTIFICATE OF CORRECTION

PATENT NO. : 9,730,673 B2
APPLICATION NO. : 14/358539
DATED : August 15, 2017
INVENTOR(S) : Sebastien Robert et al.

Page 1 of 1

It is certified that error appears in the above-identified patent and that said Letters Patent is hereby corrected as shown below:

In the Specification

Column 4, Line 36:

" $\forall n, \ 1 \leq n \leq N-1, \ \begin{cases} x_n = c_n - d_n \cdot d_n' \\ y_n = d_n \sqrt{1-(d_n')} \end{cases}$ , where "

Should read:

-- $\forall n, \ 1 \leq n \leq N-1, \ \begin{cases} x_n = c_n - d_n \cdot d_n' \\ y_n = d_n \sqrt{1-(d_n')^2} \end{cases}$ , where --.

Column 9, Line 54:

" $\forall n, \ 1 \leq n \leq N-1, \ \begin{cases} x_n = c_n - d_n \cdot d_n' \\ y_n = d_n \sqrt{1-(d_n')} \end{cases}$ , where "

Should read:

-- $\forall n, \ 1 \leq n \leq N-1, \ \begin{cases} x_n = c_n - d_n \cdot d_n' \\ y_n = d_n \sqrt{1-(d_n')^2} \end{cases}$ , where --.

In the Claims

Column 17, Line 1, Claim 6:

" $\forall n, \ 1 \leq n \leq N-1, \ \begin{cases} x_n = c_n - d_n \cdot d_n' \\ y_n = d_n \sqrt{1-(d_n')} \end{cases}$ , where "

Should read:

-- $\forall n, \ 1 \leq n \leq N-1, \ \begin{cases} x_n = c_n - d_n \cdot d_n' \\ y_n = d_n \sqrt{1-(d_n')^2} \end{cases}$ , where --.

Signed and Sealed this
Thirty-first Day of July, 2018

Andrei Iancu
*Director of the United States Patent and Trademark Office*